United States Patent [19]
Viout et al.

[11] 3,984,536
[45] Oct. 5, 1976

[54] COSMETIC COMPOSITION CONTAINING ESSENTIALLY HOMOGENEOUS VINYL ACETATE/CROTONIC ACID COPOLYMER

[75] Inventors: André Viout, Montreuil; Paul Roussopoulos, Paris; Christos Papantoniou, Epinay-sur-Seine, all of France

[73] Assignee: L'Oreal, Paris, France

[22] Filed: Feb. 19, 1975

[21] Appl. No.: 551,131

Related U.S. Application Data

[63] Continuation of Ser. No. 44,882, June 9, 1970, abandoned.

[30] Foreign Application Priority Data

June 12, 1969 Luxemburg............................ 58850

[52] U.S. Cl................................. 424/47; 8/127.51; 260/29.6 ME; 260/29.6 MN; 260/33.4 R; 424/DIG. 1; 424/DIG. 2; 424/71; 526/317; 526/319; 526/206; 526/217; 526/227; 526/232
[51] Int. Cl.².......................................... A61K 7/11
[58] Field of Search ......... 260/85.7, 33.4 R, 86.1 E; 424/DIG. 1, DIG. 2, 47, 71; 8/127.51

[56] References Cited
UNITED STATES PATENTS
2,996,471    8/1961    Reiter et al.................... 260/85.7 X OTHER PUBLICATIONS
Root et al., Drug and Cosmetic Industry, vol. 96, No. 3, Mar. 1965, pp. 327–328, 416–417 and 422–423.
David, Drug and Cosmetic Industry, vol. 97, No. 4, Oct. 1965, pp. 502–504 and 618–621.

Primary Examiner—James O. Thomas, Jr.
Assistant Examiner—Vera C. Clarke
Attorney, Agent, or Firm—Cushman, Darby & Cushman

[57] ABSTRACT

A cosmetic composition for use as a hair lacquer or hair-setting lotion contains an essentially homogeneous vinyl acetate/crotonic acid copolymer, the macromolecular chains of which contain essentially the same content of each of vinyl acetate and crotonic acid along the entire length thereof. The content of each of vinyl acetate and crotonic acid does not vary more than 2.5% by weight relative to the average content of each in essentially all of the macromolecular chains, along essentially the entire length of each of said chains.

5 Claims, No Drawings

COSMETIC COMPOSITION CONTAINING ESSENTIALLY HOMOGENEOUS VINYL ACETATE/CROTONIC ACID COPOLYMER

This is a continuation of application Ser. No. 44,882 filed June 9, 1970, now abandoned.

The present invention relates to novel cosmetic compositions such as hair-setting lacquers or lotions, and novel resins or copolymers that can be used in the formulation of these cosmetic compositions.

More particularly, the present invention relates to novel cosmetic compositions comprising a base of vinyl acetate/crotonic acid copolymers of a particular type.

Heretofore lacquers for hair or hair-setting lotions have been made by using aqueous or dilute alcoholic solutions of a vinyl acetate/crotonic acid copolymer containing a proportion of about 5 to 20% crotonic acid. Such cosmetic compositions are not totally satisfactory in practice, however, because the resulting resin films that remain on the hair after application do not have all the desired qualities. In particular, the hair is not sufficiently brilliant and the removal of the film by combing is often difficult. It has also been found difficult to make repeated applications of such aerosol lacquers, which are necessary between two settings, without causing a powdering of the resin that is on the hair.

The present invention provides a novel cosmetic composition which surprisingly and notably increases the cosmetic qualities of a vinyl acetate/crotonic acid copolymer. Such copolymers are prepared in such a manner that they have a homogeneous or essentially homogeneous composition, i.e., each of the macromolecular chains constituting the resin is characterized in that to a considerble degree it has the same proportion of vinyl acetate and crotonic acid content along the entire length of the chain.

Thus, the present invention has for its object a novel cosmetic composition such as a hair-setting lacquer or lotion, which comprises a vinyl acetate/crotonic acid copolymer, the macromolecular chains of which contain substantially the same content of each of the two constituent monomers along the entire length of the chains, the content of each of the monomers not varying more than 2.5% by weight relative to the average content of the respective monomer for essentially all of the macromolecular chains along essentially the entire length of said chains.

Such vinyl acetate/crotonic acid copolymers used in the present invention will hereafter be designated by the term "essentially homogeneous polymers".

The applicants have found that the cosmetic qualities of such copolymers are significantly and surprisingly increased when the composition of the macromolecular chains constituting the copolymer are almost identical for each of them along the entire length of each polymer chain.

It has been known, of course, to use a vinyl acetate/crotonic acid copolymer, whose overall proportion corresponds to 10% crotonic acid for 90% vinyl acetate, in the preparation of cosmetic compositions for use as hair-setting lacquers or lotions.

However, an analysis of the composition of such a copolymer reveals that the proportion of crotonic acid in the macromolecular chains varies from 0% (pure vinyl acetate) to about 21% crotonic acid. More precisely, such a copolymer comprises a mixture of polymers made up of about 6% polyvinyl acetate and 94% of a vinyl acetate/crotonic acid copolymer, the crotonic acid content of which varies between about 21% and 0%.

In contrast to such a copolymer, the applicants have surprisingly found that significantly improved results were obtained in regard to the cosmetic qualities of vinyl acetate/crotonic acid polymers, by eliminating from the copolymer pure polyvinyl acetate and by effecting in the macromolecular chains of the copolymer a crotonic acid content which does not vary more than ± 2.5% by weight from the theoretical value of 10%, i.e., a copolymer having a crotonic acid content between 7.5 and 12.5% along the entire length of the macromolecular chains.

Hair-setting lacquers and lotions formulated, in accordance with the present invention, with such essentially homogeneous copolymers provide a notable increase in the brilliance of the hair treated and a significant increase in the ease with which they can be removed from the hair by combing. Further, in the case of lacquers, it is possible, without inconvenience, to make daily superposed applications, which in present practice are not acceptable with prior art copolymers even though such prior art copolymers may have the same empirical formula as the homogeneous copolymers of the present invention.

The specific example of the novel cosmetic composition given above does not constitute a limit for the present invention, and it is clear that it is possible to depart from perfect homogeneity without causing the cosmetic qualities of the copolymer to drop sharply.

However, a copolymer having an average composition of 90% vinyl acetate and 10% crotonic acid, made up of at least 1% polyvinyl acetate and a vinyl acetate/crotonic acid copolymer, whose crotonic acid content varies between 15.87% and 0%, does not present in a cosmetic composition, the qualities achieved by the use of the essentially homogeneous copolymers of the present invention.

It has also been found that copolymers of vinyl acetate/crotonic acid which comprise a proportion of vinyl acetate and crotonic acid other than 90% and 10% respectively when made to exhibit the essential homogeneity as defined above, can also be usefully employed in the cosmetic composition of this invention. Thus, vinyl acetate/crotonic acid copolymers having a 97 to 85 percent by weight vinyl acetate content and a corresponding 3 to 15 percent by weight crotonic acid content wherein the crotonic acid content does not vary substantially more than 2.5% by weight of the chosen crotonic acid content can also be employed to give the unexpected desirable characteristics in the cosmetic composition of this invention.

The cosmetic composition, according to the present invention, can be provided in the form of a hair lacquer by admixing one or more copolymers according to the present invention with a lower alkanol such as ethyl or isopropyl alcohol and packaging this alcoholic mixture in a conventional aerosol bomb together with a liquified propellant under pressure.

For example, a sprayable aerosol hair lacquer can be provided according to this invention by adding 1 to 4% by weight of one or more copolymers defined above to a mixture made up of 25 to 33 parts by weight of an anhydrous aliphatic alcohol having 1 to 6 carbon atoms such as ethanol or isopropanol and 66 to 75 parts by weight of a liquified propellant, such as a halogenated hydrocarbon, for instance, dichlorodifluoromethane, trichlorofluoromethane and 1,2-dichlorotetrafluoromethane. Obviously, other conventionally employed aerosol propellants can also be used.

Another cosmetic composition according to the present invention can also be provided in the form of a hair-setting lotion prepared by dissolving 1 to 3% by weight of one or more of the above described copolymers in a dilute lower alkanol solution containing from 20 to 50% alcohol.

Of course, the cosmetic compositions of this invention can also include conventional cosmetic adjuvants such as plasticizers, perfumes, dyes or any other adjuvants currently used in cosmetics.

A process for preparing an essentially homogeneous vinyl acetate/crotonic acid polymer used in the cosmetic compositions of this invention can be found, for instance, in French Pat. Nos. 1,090,912 and 1,002,763 and such process does not form any part of the present invention. As a brief summary of the known procedures conventionally employed to produce such essentially homogeneous polymers, the following description is provided.

A suspension of a mixture of vinyl acetate monomer and crotonic acid is prepared having a proportion of vinyl acetate to crotonic acid such that there is produced, at the beginning of polymerization, a copolymer having a predetermined proportion of said reactants. The polymerization is then initiated. To the suspension there is added a predetermined amount of crotonic acid, until the content of crotonic acid in the suspension of monomers corresponds to the formation of a copolymer whose crotonic acid content exceeds the limits that have been predetermined. The polymerization is then allowed to continue and the process is repeated until a calculated consumption of the vinyl acetate occurs. The polymerization is stopped at the desired polymerization stage by introducing a small amount of an aqueous solution of a polymerization inhibitor, such as, for example, hydroquinone.

Further, the process for making the essentially homogeneous copolymer can also include constantly measuring the resistivity of the reaction medium, thereby determining at any time during the reaction the amount of the most reactive monomer to be introduced into the reaction medium, this determination being dependent upon the variation of the resistivity measured.

Actually, the measurement of the resistivity of the reaction medium makes it possible to determine with a good approximation the amount of copolymer formed in this medium, because of the established relationship between the resistivity and the amount of polymer formed, or rate of polymerization.

Moreover, the resistivity depends on the amount and to a certain extent on the nature of this polymer formed. Consequently, in the case of a polymerization controlled from its initial stage, it is possible to know at each instant the exact composition of the polymer being formed and thereby the specific resistivity of the copolymer formed. A determination of the latter makes it possible to eliminate by a known relation the variable which constitutes the specific resistivity of the copolymer.

Therefore, this process makes possible, by knowing at each instant the variation of the characteristics of the reaction medium, the determination of the suitable instant delivery of the most reactive monomer to be added.

Catalysts conveniently employed to effect the polymerization reaction include those conventionally used for polymerization of unsaturated monomers. Benzoyl peroxide, azobisisobutyronitrile and peroxide catalysts in general can be employed.

The molecular weight of the copolymers obtained can also be regulated by addition of small amounts, i.e. about 0.15 to 0.8 by weight, of conventional chain regulating agents, such as chloroform, bromoform, carbon tetrabromide and carbon tetrachloride. The molecular weight of the homogeneous copolymers obtained and used for the completion of the novel cosmetic composition is generally between 10,000 to 100,000.

Usually, the polymerization reaction is performed under isothermal conditions and in suspension or in solution.

For a better understanding of the invention, there will now be described, by way of illustration, two examples of cosmetic composition according to the invention as well as an example of preparation of an essentially homogeneous vinyl acetate/crotonic acid copolymer.

EXAMPLE A

Preparation of an essentially homogeneous vinyl acetate/crotonic acid copolymer

Into a 1-liter flask provided with mechanical stirring, a nitrogen intake, a thermometer and a bromine funnel there are introduced 192.77 g of vinyl acetate, 7.77 g crotonic acid, 4.4 g of 88% benzoyl peroxide, and 0.6 g hydroxy ethyl cellulose in solution in 200 ml of water saturated with 74.6 g of sodium chloride.

This reaction mixture is heated with stirring and there are introduced by means of the bromine funnel 102 g of an aqueous solution containing 12.23 g of crotonic acid. Introduction of the crotonic acid is performed in 400 minutes and the rate of introduction is such that the copolymer being formed constantly contains 90.4 ± 0.4% vinyl acetate and 9.6 ± 0.4% crotonic acid.

Copolymerization occurs at reflux temperature of the vinyl acetate-water azeotrope (68°C) according to the standard technique of polymerization in suspension. The presence of an excess of 33.4 g of sodium chloride in the initial reaction mixture is essential to saturate the water later introduced in form of an aqueous crotonic acid solution.

Polymerization is terminated when the degree of polymerization reaches 85%, by the introduction of 4 ml of an aqueous solution containing 0.008 g of hydroquinone. The vinyl acetate which has not yet reacted is eliminated by distillation. The crotonic acid which has not yet reacted is eliminated by washing of the resulting beads with water.

The acid index of the copolymer obtained is equal to 64 (the theoretical index being 65).

The relative viscosity of the resulting copolymer, measured in a 5% solution in DMF at 34.6°C. by means of a Baume type capillary tube, is 2.78 cp.

The average mass by weight in methanol solution was also determined by a photogoniodiffusometer (model 42000, marketed by the Company SOFICA) and measured 56,000.

Other essentially homogeneous vinyl acetate/crotonic acid copolymers having different weight proportions of vinyl acetate and crotonic acid are prepared in essentially the same manner.

EXAMPLE 1

A hair lacquer composition according to the present invention is prepared by providing a solution of:

| | |
|---|---|
| Homogeneous copolymer prepared according to Example A | 8 g |
| 2-Amino-2 methyl-1,3-propanediol | 0.797 g |
| Ethyl alcohol sufficient for | 100 g |

25 g of this solution are put in an aerosol bomb with 45 g of the liquified propellant gas, trichloromonofluoromethane and 30 g of the liquified propellant gas, dichlorodifluoromethane.

This lacquer was sprayed on hair imparting to the same a brilliant sheen. Further, the hair did not exhibit any sticky characteristics.

Further, it was observed that the lacquer could easily be removed simply by brushing the hair. Additionally repeated applications of the hair lacquer to the hair did not produce any significant diminution in the desirable cosmetic properties imparted thereto.

EXAMPLE 2

A hair-setting lotion, according to the present invention, having the following composition is prepared:

| | |
|---|---|
| Homogeneous polymer prepared according to Example A | 2 g |
| 2-Amino-2 methyl-1-propanol | 0.237 g |
| Isopropyl alcohol | 45 cc |
| Water, sufficient for | 100 cc |

The hair setting lotion is applied to hair and imparts thereto a non-sticky film which does not powder and which gives the hair a beautiful luster.

What is claimed is:

1. A sprayable hair lacquer cosmetic composition packaged under pressure in an aerosol container, said composition comprising 2-amino-2-methyl-1,3-propanediol or 2-amino-2-methyl-1-propanol, a lower alkanol selected from the group consisting of ethyl alcohol and isopropyl alcohol, a solution of an essentially homogeneous copolymer of 3–15 weight percent crotonic acid and 97–85 weight percent vinyl acetate, the macromolecular chains of said copolymer containing essentially the same content of each of vinyl acetate and crotonic acid along the entire length thereof, said content of each of the vinyl acetate and crotonic acid varying not more than 2.5 percent by weight relative to the average content of said vinyl acetate and crotonic acid in essentially all of the macromolecular chains, along essentially the entire length of each of said chains, said copolymer having a molecular weight ranging between 10,000 and 100,000, said copolymer being present in amounts of 1 to 4 percent by weight of said composition, and a liquefied propellant gas in admixture with said lower alkanol, said lower alkanol being present in amounts of 25 to 33 parts by weight and said propellant gas being present in amounts of 66 to 75 parts by weight of said admixture.

2. A cosmetic hair-setting lotion composition comprising in an aqueous solution of 2-amino-2-methyl-1,3-propanediol or 2-amino-2-methyl-1-propanol, a lower alkanol selected from the group consisting of ethyl alcohol and isopropyl alcohol, said solution containing 20 to 50 percent by weight of said lower alkanol, a solution of an essentially homogeneous copolymer of 3–15 weight percent crotonic acid and 97–85 weight percent vinyl acetate, the macromolecular chains of said copolymer containing essentially the same content of each of vinyl acetate and crotonic acid along the entire length thereof, said content of each of the vinyl acetate and crotonic acid varying not more than 2.5 percent by weight relative to the average content of said vinyl acetate and crotonic acid in essentially all of the macromolecular chains, along essentially the entire length of each of said chains, said copolymer having a molecular weight ranging between 10,000 and 100,000, said copolymer being present in amounts of 1 to 3 percent by weight of said composition.

3. An essentially homogeneous 97–85 weight percent vinyl acetate/ 3–15 weight percent crotonic acid copolymer, the macromolecular chains of which contain essentially the same content of each of vinyl acetate and crotonic acid units along the entire length thereof, said content of each of the vinyl acetate and crotonic acid units varying not more than 2.5% by weight relative to the average content of said vinyl acetate and crotonic acid in essentially all macromolecular chains along essentially the entire length of each of said chains, having a molecular weight ranging between 10,000 and 100,000.

4. The homogeneous vinyl acetate/crotonic acid copolymer of claim 3 wherein the crotonic acid content is between 3 to 13% by weight and does not vary more than 2.5% by weight along essentially the entire length of each of the chains.

5. The homogeneous vinyl acetate/crotonic acid copolymer of claim 3 wherein the crotonic acid content along essentially the entire length of each of the chains has value equal to 10% ± 2.5% by weight.

* * * * *